United States Patent [19]
Chiu-Hsiung et al.

[11] Patent Number: 5,704,923
[45] Date of Patent: Jan. 6, 1998

[54] LIQUID LEVEL DETECTOR AND ALARM DEVICE FOR DRIP INFUSION SETS

[76] Inventors: Chiang Chiu-Hsiung, 5Fl., No.3, Alley 4, Lane 279, Li Hung St., Pei-Tou, Taipei, Taiwan; Kao Han-Chin, No. 56, Da-Long St., Taipei, Taiwan

[21] Appl. No.: 522,440

[22] Filed: Aug. 31, 1995

[51] Int. Cl.⁶ .................................................. A61M 1/00
[52] U.S. Cl. .................................................. 604/260
[58] Field of Search .......................... 604/253, 255, 604/260, 407, 246; 128/DIG. 13

[56] References Cited

U.S. PATENT DOCUMENTS

| | | | |
|---|---|---|---|
| 3,588,859 | 6/1971 | Petree | 604/246 |
| 3,605,741 | 9/1971 | Spencer | 604/246 |
| 4,223,231 | 9/1980 | Sugiyama | 604/246 |
| 4,532,936 | 8/1985 | LeVeen et al. | 604/246 |
| 4,820,281 | 4/1989 | Lawler, Jr. | 604/253 |
| 5,186,057 | 2/1993 | Everhart | 604/253 |
| 5,267,978 | 12/1993 | Dirr, Jr. | 604/253 |
| 5,346,466 | 9/1994 | Yerlilkay et al. | 604/253 |

*Primary Examiner*—Manuel Mendez
*Attorney, Agent, or Firm*—Donald C. Casey

[57] ABSTRACT

A liquid level detector and alarm device including an electrical bridge consisting of two infrared detectors for detecting the change of the liquid level of the infusion solution of a drip infusion set, an A/D converter, and a single chip microprocessor connected to the electrical bridge through the A/D converter and controlled by the electrical bridge to drive a buzzer when the liquid level drops below a predetermined value.

1 Claim, 5 Drawing Sheets

FIG. 6A
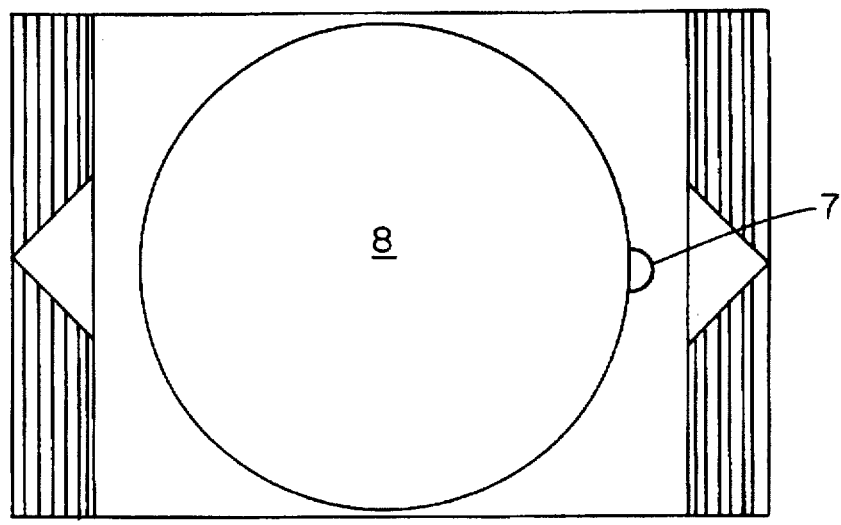
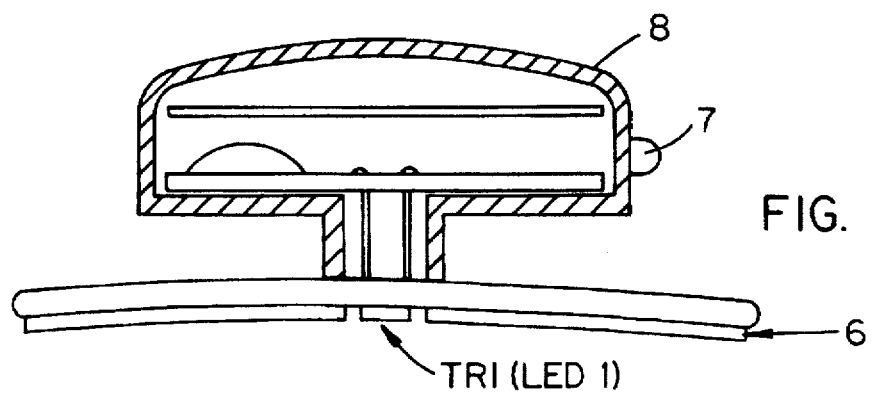
FIG. 6B
FIG. 6C
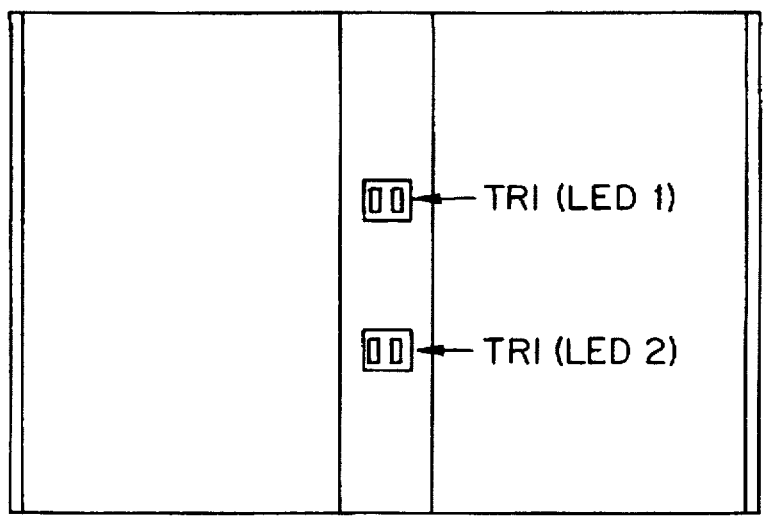

LIQUID LEVEL DETECTOR AND ALARM DEVICE FOR DRIP INFUSION SETS

BACKGROUND OF THE INVENTION

The present invention relates to a liquid level detector and alarm device for installation in the bottle of a drip infusion set to detect the liquid level, and to give an audio alarm when the liquid level drops below a predetermined value.

When a drip infusion set is used for the introduction of a saline or other solution into a vein to treat the patient, the nurse must frequently review the liquid level of the solution so that the infusion can be stopped before the solution is fully consumed. In case the infusion is not stopped when the solution is fully consumed, a reverse flow of blood or the introduction of air into the vein may occur. There are known various monitoring apparatus for automatically monitoring drip infusion. These monitoring apparatus give an audio alarm signal when detect no drips of solution within a predetermined length of time. However, these monitoring apparatus are commonly heavy and expensive.

SUMMARY OF THE INVENTION

According to the preferred embodiment of the present invention, the liquid level detector and alarm device comprises a mounting device for adhering to the side wall of the bottle of a drip infusion set, an electrical bridge, which includes two infrared detectors for detecting the liquid level of the infusion solution in the bottle of the drip infusion set, an analogue/digital converter, which converts the output value of the electrical bridge into a digital signal, a single chip microprocessor, which receives the digital signal from the analogue/digital converter and compares it with an initial output value obtained from the said electrical bridge, a buzzer controlled by the single chip microprocessor to buzz when the comparison between the digital signal from the analogue/digital converter and the initial output value from the electrical bridge shows a difference, and a press button, which drives the single chip microprocessor to record the initial output value of the electrical bridge when depressed once, or stops the buzzer from operation when depressed twice.

BRIEF DESCRIPTION OF THE DRAWINGS

FIG. 6A is a front view of the detector and alarm device of the present invention;

FIG. 6B is a top view in partial section of the device of FIG. 6A; and

FIG. 6C is a rear view of the device of FIG. 6A.

DETAILED DESCRIPTION OF THE PREFERRED EMBODIMENT

Figure 1:
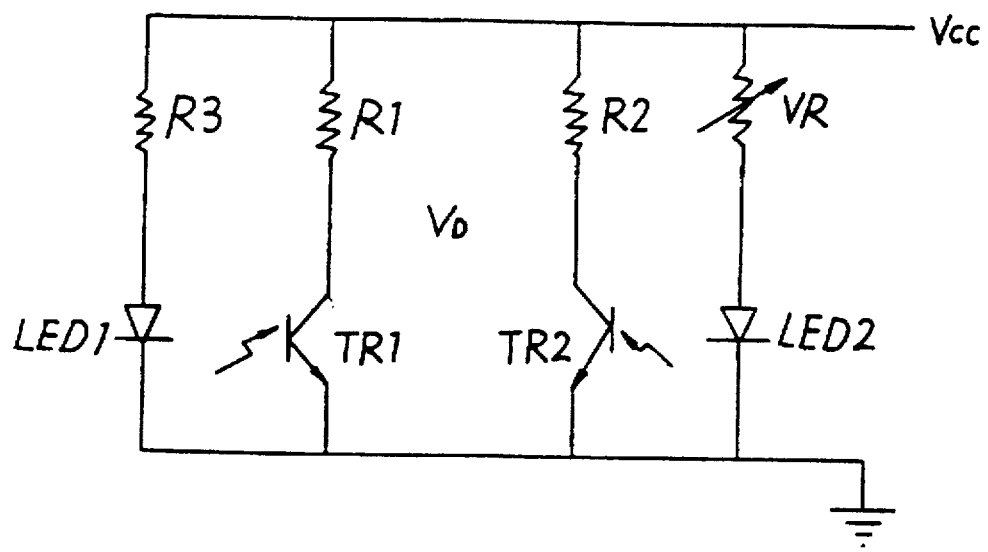
FIG. 1 is a circuit diagram of an electrical bridge according to the present invention.

Referring to FIG. 1, LED 1 and TR 1 form a first infrared detector, LED 2 and TR 2 form a second infrared detector. The infrared detectors incorporate with peripheral resistors to form an electrical bridge. Variable resistor VR is for adjusting the brightness of LED to balance the electrical bridge, i.e., to let the output value VD of the electrical bridge be approximately equal to zero. The electrical bridge is free from the interference of the change of external light and the interference of the change of voltage. TR 1 and TR 2 receive infrared light from LED 1 and LED 2, and can be affected by external light. Because the change of external light is reflected upon TR 1 and TR 2, the amount of change at TR 1 and TR 2 is corresponding to the variation of external light. The output signal of the electrical bridge is obtained from TR 1 and TR 2 subject to the variation of external light, the interference of external light is eliminated. Furthermore, the variation of voltage is also reacted upon TR 1 and TR 2, the electrical bridge eliminates the interference of the variation of voltage. Therefore, the operation of the electrical bridge is free from the interferences of unstable voltage and variable external light.

Figure 2:
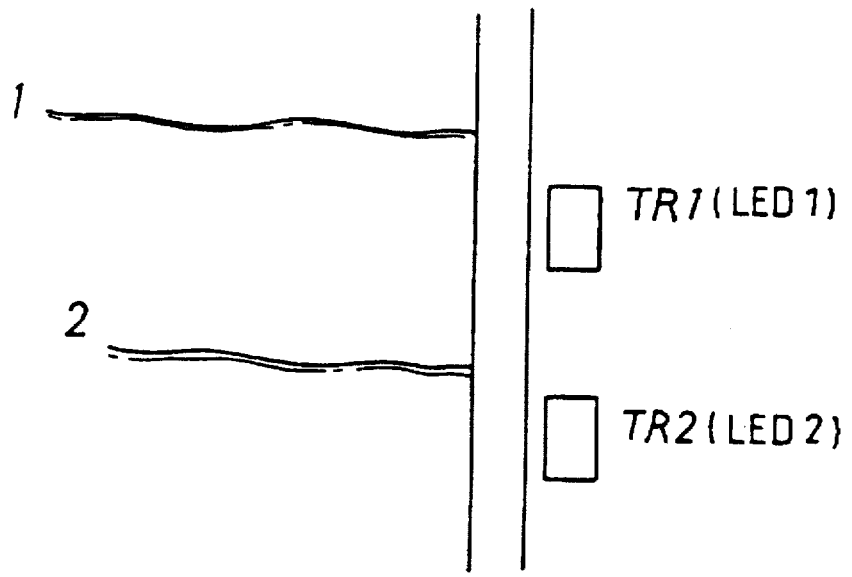
FIG. 2 shows the relationship between the infrared detectors and the liquid level according to the present invention.

FIG. 2 shows the relationship between the infrared detectors and the liquid level. When the level of the infusion solution is at level 1, infrared light is reflected by the infusion solution and received by the infrared detectors, and the electrical bridge of FIG. 1 is balanced, therefore the output value of the electrical bridge is maintained unchanged. When the level of the infusion solution drops to level 2, TR 1 receives a variation of light, the electrical bridge of FIG. 1 becomes unbalanced, therefore the output value of the electrical bridge is changed. However, because the surface of the bottle of the drip infusion set has a curvature, the electrical bridge may be unbalanced when the liquid level detector and alarm device is closely attached to the bottle. This problem must be eliminated. The present invention uses a single chip microprocessor to eliminate this problem.

Figure 3:
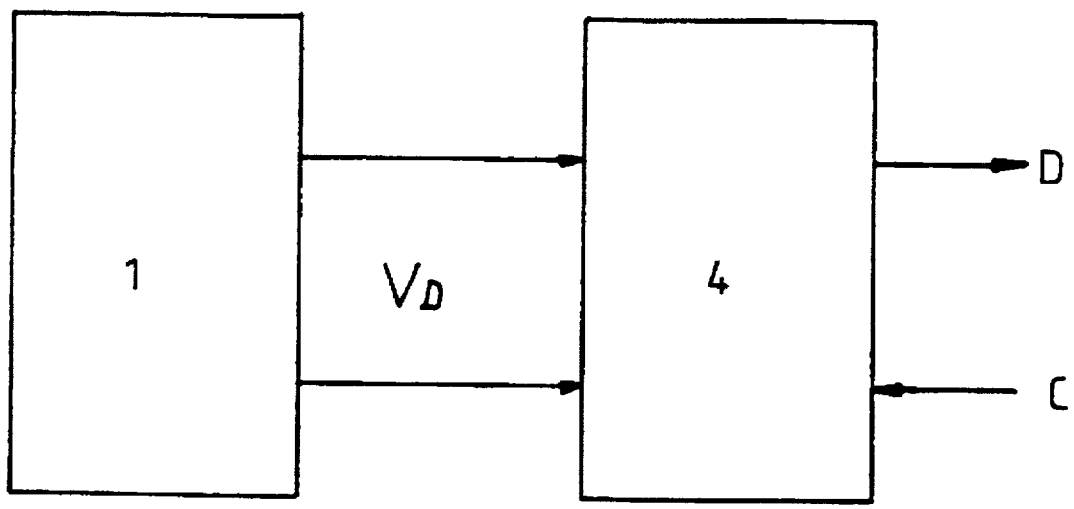
FIG. 3 shows the relationship between the single chip microprocessor and the electrical bridge according to the present invention.

Referring to FIG. 3, a single chip microprocessor 4 is installed in the liquid level detector and alarm device and connected to the electrical bridge 1. When the command of an initial value C is given to the single chip microprocessor 4, the single chip microprocessor 4 records the initial output value of the electrical bridge 1. When the output value of the electrical bridge 1 is changed with the reducing of the liquid level, the single chip microprocessor 4 compares the recorded initial value with the current output value of the electrical bridge 1. When a difference D is obtained from the comparison, the single chip microprocessor 4 immediately gives a signal to turn on a buzzer.

Figure 4:
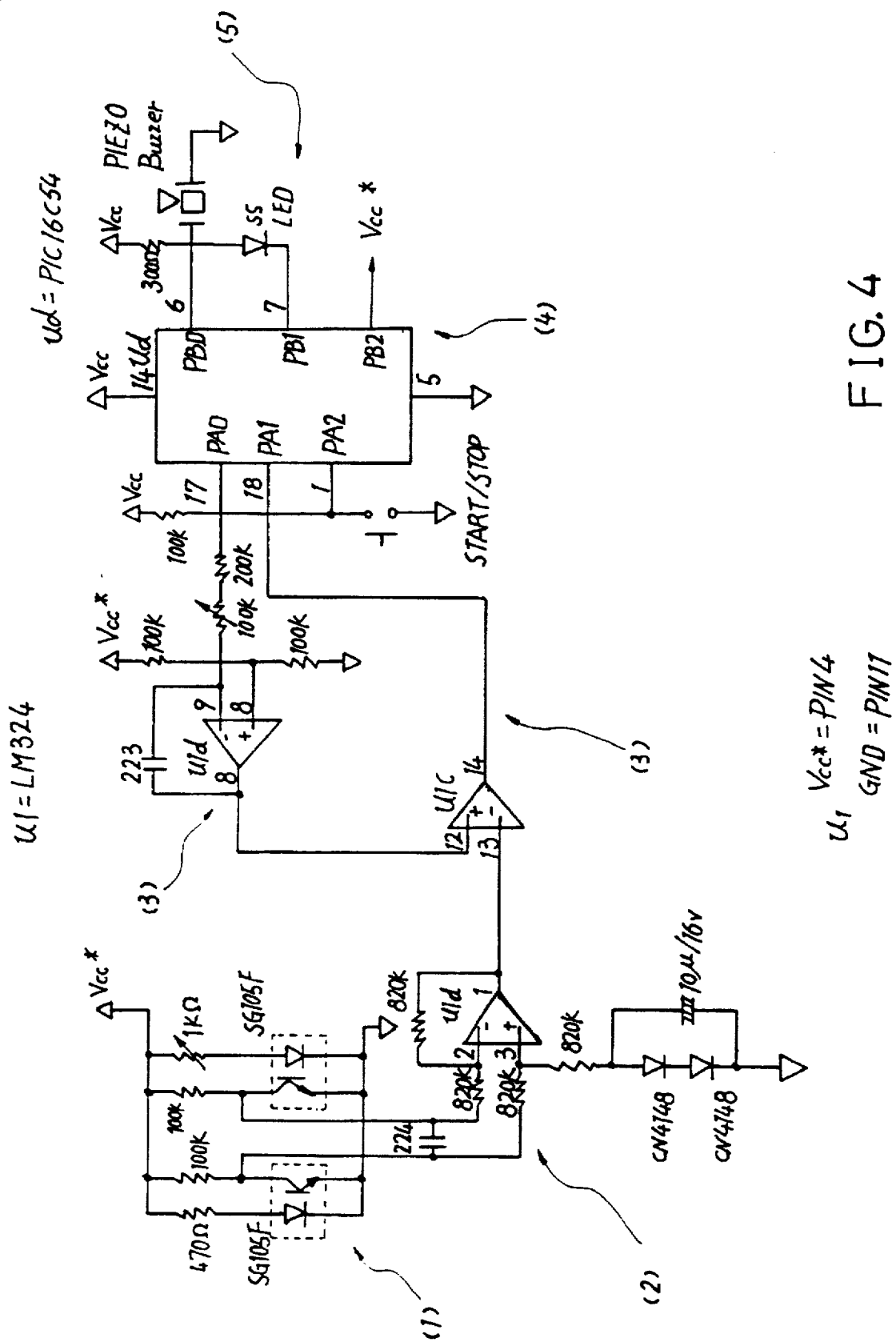
FIG. 4 is a circuit diagram of the liquid level detector and alarm device according to the present invention.
Figure 5:
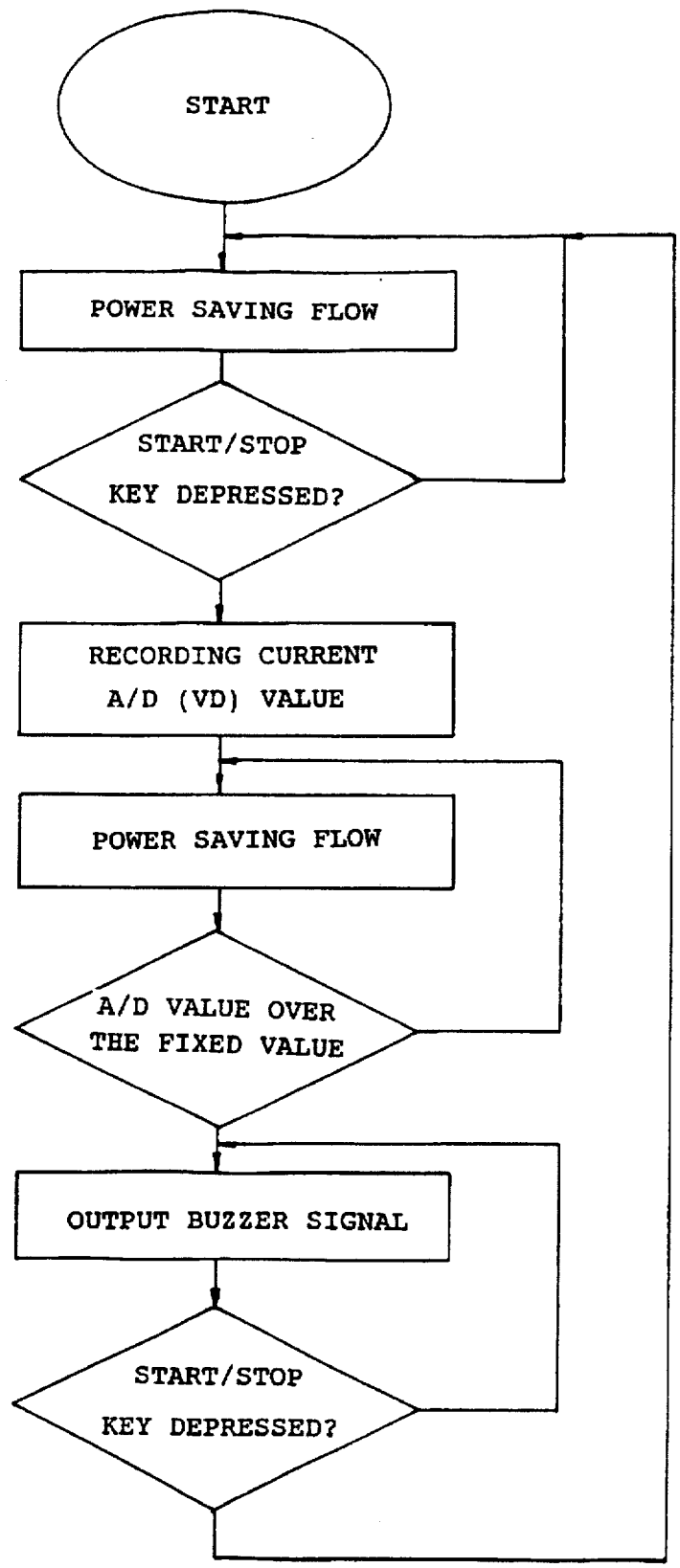
FIG. 5 is a flow chart of the software program according to the present invention.

FIG. 4 shows the circuit diagram of the liquid level detector and alarm device, in which the reference number 1 indicates the electrical bridge; the reference number 2 indicates a circuit for converting the output difference obtained from the electrical bridge 1 into a corresponding analogue signal; the reference number 3 indicates an analog/digital converter for converting the analogue signal thus obtained into a digital signal; the reference number 4 indicates the single chip microprocessor; the reference number 5 indicates the buzzer. The software flow chart of the circuit is shown in FIG. 5.

FIG. 6 shows the top view, front view, and bottom view of the liquid level detector and alarm device. The device has a mounting means 6 at the bottom side for adhering to the bottle of the drip infusion set, and a press button 7 on housing 8 for operation controls. When the press button 7 is depressed once, the single chip microprocessor is driven to record the initial output value of the electrical bridge. When the press button 7 is depressed twice, the buzzer is stopped.

It is to be understood that the drawings are designed for purposes of illustration only, and are not intended as a definition of the limits and scope of the invention disclosed.

We claim:

1. A liquid level detector and alarm device for monitoring the infusion solution in the reservoir bottle of a drip infusion set, comprising:

a housing and mounting means thereon for fastening said housing to the side wall of said reservoir bottle of said drip infusion set;

an electrical bridge contained within said housing including a first infrared detector means and a second infrared detector means for detecting the liquid level of an infusion solution in said reservoir bottle and peripheral resistors for normally establishing a voltage output from said bridge of zero, said first and second infrared detector means comprising mutually vertically spaced first and second LED-TR infrared light brightness detectors as voltage sources to thereby drive said electrical bridge to change its output value subject to the change of the liquid level of the infusion solution whereby said change will occur when the liquid level drops below one of said first and second vertically spaced LED-TR detectors;

analogue/digital converter means for converting the output value of said electrical bridge into a digital signal and for generating said signal, said converter being coupled to said bridge;

single chip microprocessor means coupled to said converter for receiving digital signals from said analogue/digital converter and for comparing said signals with an initial output value obtained from said electrical bridge;

buzzer means controlled by said single chip microprocessor means for buzzing when the comparison between the digital signal from said analogue/digital converter and the initial output value from said electrical bridge are different; and press button means coupled to said microprocessor means, for driving said single chip microprocessor means to record the initial output value of said electrical bridge when depressed once, and to stop said buzzer from operating when depressed twice.

* * * * *